United States Patent [19]
Heath et al.

[11] Patent Number: 5,958,894
[45] Date of Patent: Sep. 28, 1999

[54] AMPHIPHILIC BIGUANIDE DERIVATIVES

[75] Inventors: Timothy D. Heath; Igor Solodin, both of Madison, Wis.; Jinkang Wang, San Francisco; Yi-Lin Zhang, San Mateo, both of Calif.

[73] Assignee: Megabios Corporation, Burlingame, Calif.

[21] Appl. No.: 08/825,854

[22] Filed: Apr. 4, 1997

[51] Int. Cl.$^6$ .................................... A61K 48/00
[52] U.S. Cl. ................. 514/44; 514/2; 435/69.1; 435/320.1; 435/325; 435/455; 435/458
[58] Field of Search ..................... 435/458, 455, 435/320.1, 325, 326, 333, 377, 320, 69.1; 514/44, 2

[56] References Cited

U.S. PATENT DOCUMENTS

| | | | |
|---|---|---|---|
| 5,264,618 | 11/1993 | Felgner et al. | 560/244 |
| 5,334,761 | 8/1994 | Gebeyehu et al. | 564/197 |
| 5,550,289 | 8/1996 | Eppstein et al. | 564/293 |

FOREIGN PATENT DOCUMENTS

| | | |
|---|---|---|
| WO93/12756 | 7/1993 | WIPO . |
| WO95/14381 | 6/1995 | WIPO . |
| WO96/40962 | 12/1996 | WIPO . |
| WO96/40963 | 12/1996 | WIPO . |

OTHER PUBLICATIONS

Osterloh (Chemical Abstracts, vol. 56, 13504a, May 1962.
Wheeler et al. (Biochim. et Biophsica Acta 1280, 1996, 1–11).
Zelphati et al. (J Controlled Release 41, 99–119, 1996).
David et al., Biochimica et Biophsica Acta, 1212, 167–175, 1994.
Ledley (Human Gene Ther. (1995) 6:1129–1144).
Alton et al., (1993), *Nat. Genet.*, vol. 5, pp. 135–142.
Curd and Rose, (1946), *J. Chem. Soc.*, pp. 729–737.
Debs et al., (1990), *J. Biol. Chem.*, vol. 265, pp. 10189–10192.
Emich, F., *Monatsh. Chem.*, vol. 1891, No. 12, pp. 5–29.
Farhood et al., (1992), *Biochim. Biophys. Acta*, vol. 1111, pp. 239–246.
Felgner et al., (1987), *Proc. Natl. Acad. Sci. (USA)*, vol. 84, pp. 7413–7417.
Felgner et al., (1994), *J. Biol. Chem.*, vol. 269, No. 4, pp. 2550–2561.
Hazinski et al., (1991), *Am. J. Resp. Cell Molec. Biol.*, vol. 4, pp. 206–209.
Hofland et al., (1996), *Proc. Natl. Acad. Sci. (USA)* vol. 93, pp. 7305–7309.
Krentzberger and Tantaway, (1977), *Liegis Ann. Chem.*, pp. 1625–1632.
Lasic and Templeton, (1996), *Adv. Drug Deliv. Rev.* 20, pp. 221–266.
Malone et al., (1989), *Proc. Natl. Acad. Sci. (USA)*, vol.86, pp. 6077–6081.
Nabel et al., (1990), *Science*, vol. 249, pp. 1285–1288.
Perales et al., (1994), *Eur. J. Biochem.*, vol. 226, pp. 255–266.
Rose et al., (1991), *BioTechniques*, vol. 10, No. 4, pp. 520–525.
Stribling et al., (1992) *Proc. Natl. Acad. Sci. (USA)*, vol. 89, pp. 11277–11281.
Vigneron et al., (1996), *Proc. Natl. Acad. Sci. (USA)*, vol. 93, pp. 9682–9686.
von der Leyen et al., *Proc. Natl. Acad. Sci. (USA)*, vol. 92, pp. 1137–1141.
Wang and Huang, (1987), *Proc. Natl. Acad. Sci. (USA)*, vol. 84, pp. 7851–7855.
Warner and Lynch, (1979), *J. Med. Chem.*, vol. 22, No. 4, pp. 359–366.
Warner et al., (1976), *J. Pharm. Sci.*, vol. 65, pp. 1070–1072.
Wolff et al., (1990), *Science*, vol. 247, pp. 1465–1468.
Wu and Wu, (1988), *J. Biol. Chem.*, vol. 263, pp. 14621–14624.
Yoshimura et al., (1992), *Nucl. Acids Res.*, vol. 20, pp. 3233–3240.
Zhu et al., (1993), *Science*, vol. 261, pp. 209–211.

*Primary Examiner*—Bruce R. Campbell
*Assistant Examiner*—Dave Trong Nguyen
*Attorney, Agent, or Firm*—McDonnell, Boehnen, Hulbert & Berghoff

[57] ABSTRACT

Cationic derivatives of biguanide are provided, which are useful in the preparation of lipid carriers for mediating transfection of mammalian cells in vivo and in vitro.

21 Claims, No Drawings

AMPHIPHILIC BIGUANIDE DERIVATIVES

FIELD OF THE INVENTION

This invention relates to cationic lipids for use in the preparation of liposomes and other lipid-containing carriers of nucleic acids and other substances, for delivery to cells in vitro or in vivo.

BACKGROUND OF THE INVENTION

A number of lipid-based materials such as liposomes have been used as biological carriers for many pharmaceutical and other biological applications, particularly to introduce drugs, radiotherapeutic agents, enzymes, viruses, transcriptional factors and other cellular vectors into a variety of cultured cell lines and animals. Clinical trials have demonstrated the effectiveness of liposome-mediated drug delivery for targeting liposome-entrapped drugs to specific tissues and specific cell types. See, for example, U.S. Pat. No. 5,264,618, which describes techniques for using lipid carriers, including the preparation of liposomes and pharmaceutical compositions and the use of such compositions in clinical situations. More recently, cationic lipids have been used to deliver genes to cells, allowing efficient uptake and expression of foreign genes. While the basic methodology for using lipid-mediated vectors is well established, however, improvements in the materials used in the methods, both in terms of biocompatibility and in terms of effectiveness of the delivery process, are still desirable.

In particular, lipid-mediated delivery of exogenous nucleic acids in vivo in humans and/or various commercially important animals will ultimately permit the prevention, amelioration or cure of many important diseases and the development of animals with commercially important characteristics. The exogenous genetic material, either DNA or RNA, may provide a functional gene which, when expressed, produces a protein lacking in the cell or produced in insufficient amounts, or may provide an antisense RNA or ribozyme to interfere with a cellular function, e.g. a virus or cancer.

Nucleic acids are generally large polyanionic molecules which, therefore, bind cationic lipids through charge interactions. Lipid carriers have been shown to enhance gene delivery in vitro and in vivo. It is believed that positive charges of the lipid/DNA complexes mediate binding to negatively charged cellular membranes. By complexing with lipid carriers, DNA is protected from nucleases, enhancing receptor-mediated uptake and expression in the tissues and cells of interest. Felgner et al., (1994) J. Biol. Chem. 269(4):2550–2561. Typically, cationic lipids are mixed with neutral lipids, which allows the formation of stable liposomes. The liposomes are then complexed with nucleic acid, i.e., DNA, RNA or combinations of the two. Alterations in the lipid formulation allow targeting of DNA to different tissues in vivo. PCT patent application numbers WO 96/40962 and WO 96/40963. For in vivo applications, it is also desirable that the lipid carriers be biodegradable by the host, particularly with respect to treatment regimens that involve repeat administrations.

Relevant Literature

Literature describing the use of lipids as carriers for DNA include the following: Zhu et al., (1993) Science, 261:209–211; Vigneron et al., (1996) Proc. Natl. Acad. Sci. U.S.A., 93:9682–9686; Hofland et al., (1996) Proc. Natl. Acad. Sci. U.S.A., 93:7305–7309; Alton et al., (1993) Nat. Genet. 5:135–142; von der Leyen et al., (1995) Proc. Natl. Acad. Sci. (U.S.A.), 92:1137–1141; Nabel, et al., (1990) Science, 249: 1285–1288; Hazinski, et al., (1991) Am J. Resp. Cell Molec. Biol., 4:206–209; and Wang and Huang (1987) Proc. Natl. Acad. Sci. (U.S.A.), 84:7851–7855. For a review of liposomes in gene therapy, see Lasic and Templeton, (1996) Adv. Drug Deliv. Rev. 20:221–266.

Ligand-specific, cation-based DNA delivery systems are described in Wu and Wu (1988) J. Biol. Chem., 263:14621–14624; for review see Perales et al., (1994) Eur. J. Biochem. 226: 255–266, and references cited therein. Naked DNA expression vectors are described in Nabel et al., (1990), supra, and Wolff et al., (1990) Science, 247:1465–1468. Direct injection of DNA into tissue producing localized expression is described in Nabel (1990) supra; and Hazinski et al., (1991), supra. See also Stribling et al., (1992) Proc. Natl. Acad. Sci (U.S.A.) 89:11277–11281, which reports the use of lipids as carriers for aerosol gene delivery to the lungs of mice, and Yoshimura et al., (1992) Nucl. Acids Res., 20:3233–3240.

Cationic lipid carriers have been shown to mediate intracellular delivery of plasmid DNA (Felgner et al., (1987) Proc. Natl. Acad. Sci. (U.S.A.), 84:7413–7416); mRNA (Malone et al., (1989) Proc. Natl. Acad. Sci. (U.S.A.) 86:6077–6081); and purified transcription factors (Debs et al., (1990) J. Biol. Chem. 265:10189–10192), in functional form. Cationic lipid formulations for DNA delivery to particular tissues is described in PCT patent application numbers WO 96/40962 and WO 96/40963.

Certain aryl biguanide compounds are described in Warner and Lynch, (1979) J. Med. Chem., 22(4):359–366. Synthesis of biguanide derivatives is described in Warner et al., (1976) J. Pharm. Sci., 65:1070.

SUMMARY OF THE INVENTION

Novel amphiphilic lipids comprising a biguanide group are provided, as are their methods of use. The amphiphiles are capable of forming complexes with nucleic acids, and other biological compounds, and the complexes are capable of transforming mammalian cells.

DESCRIPTION OF SPECIFIC EMBODIMENTS

Amphiphilic derivatives of biguanide are provided, which are useful as carriers for biologically active molecules such as antibiotics or nucleic acids used in cell transformation processes. The compounds are particularly useful in the preparation of lipid carriers for nucleic acid delivery, mediating mammalian cell transfection in vitro and in vivo. The amphiphiles of the invention are characterized by the presence of a positively charged biguanide head group. Since biguanide is strongly basic ($pK_a$ 11.5), it remains protonated over a wide range of pH and is, therefore, relatively insensitive to pH variations during in vitro lipid-nucleic acid complexation processes.

The amphiphiles of the invention are also useful in any of the several applications in which cationic lipids find use. For example, they may be used in standard drug delivery regimens, such as for the aerosolized delivery of antibiotics to the lungs of patients, or the topical application of various pharmaceutical formulations of creams, pastes, gels and the like.

Cationic lipids useful for gene delivery typically consist of a hydrophilic polar head group and lipophilic aliphatic chains. Alternatively, cholesterol derivatives having a cationic polar head group are used in a similar manner. Farhood et al., (1992) Biochim. Biophys. Acta 1111:239–246; Vigneron et al., (1996) Proc. Natl. Acad. Sci. (U.S.A.) 93:9682–9686. The cationic lipids, usually mixed with equimolar amounts of a neutral lipid such as dioleoylphosphatidylethanolamine (DOPE) or cholesterol, form positively charged liposomes that bind polyanionic molecules such as DNA, forming complexes that are able to mediate delivery to target cells in vitro and in vivo.

For in vivo use, for example in vivo gene therapy, it is important that the lipid carriers are metabolizable by the host organism, thus allowing repeat administrations without lipid accumulation. Thus, replacement of non-metabolizable C—N linkage bonds (e.g., DDAB (Rose et al., (1991) BioTechniques 10(4):520–525)) or ether bonds (e.g., DOTMA (U.S. Pat. No. 5,550,289)) is desirable.

It will be apparent that the cations of the invention must be present in association with one or more anions, e.g., hydroxide, chloride, bromide or more complex organic anions or bases. The particular anion associated with an amphiphilic cation is not critical to the formation or utility of the amphiphilic cation and may exchange (in whole or in part) for other anions during use of the composition. Accordingly, the amphiphilic compounds of the invention are described in this specification generally in terms of the cation without reference to any particular anion. A number of specific examples are given, however, as well as general guidance for selection of anions. For human administration, chloride is the preferred ion; also acceptable are bromide or other physiologically acceptable anions including acetate, succinate and citrate.

The invention particularly relates to novel amphiphiles having a biguanide group of the formula:

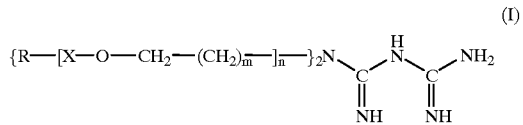

(I)

wherein each R independently is a straight-chain or branched-chain, aliphatic hydrocarbyl group of 5 to 29 carbon atoms inclusive, each X is —CH$_2$— or —CO—, each m is an integer from 0 to 7 inclusive and each n is zero or 1, with the proviso that when n is 1, the total number of carbon atoms in R and —(CH$_2$)$_m$— is at least 10, and when n is zero, each R independently is a straight-chain or branched-chain, aliphatic hydrocarbyl group of at least 10 carbon atoms inclusive. Preferred derivatives of the above formula I are those wherein n is 1. Also preferred are those compounds of formula I wherein m is from 1 to 5 inclusive, most preferably 1. Also preferred are those derivatives wherein X is —CO— and each R has from 10 to 23 carbon atoms inclusive. The R groups are saturated or unsaturated, having one or more ethylenically unsaturated linkages and may be the same or different from each other.

Illustrative R groups, taken together with the —CO— group to which it is attached (i.e. R—CO—) include lauroyl, myristoyl, palmitoyl, stearoyl, linoleoyl, oleoyl, phytanoyl, eicosanoyl, tricosanoyl and nonacosanoyl (derived from the fatty acids of the corresponding name: lauric, myristic, etc.). Alternatively, X can be —CH$_2$—. When given system names for the R groups alone, the corresponding names of the hydrocarbyl group derived from lauric acid is undecyl; from myristic acid, tridecyl; from palmitic acid, pentadecyl; from stearic acid, heptadecyl; from linoleic acid, cis, cis-8, 11-heptadecydienyl; from eicosanoic acid, nonadecyl; from tricosanoic acid, decosanyl; and from nonacosanoic acid, octacosanyl. This grouping of R groups is preferred when n is 1.

When n is zero, R is preferably the entire hydrocarbyl portion of a fatty alcohol, such as lauryl, stearyl, or myristyl group. Thus, when n is zero, the compounds of formula I are of the formula:

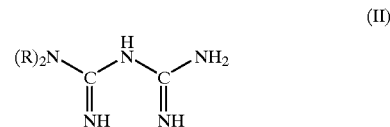

(II)

wherein R has the previously stated meaning. Thus, illustrative compounds of the above formula II are N,N-distearylbiguanide, N,N-dilaurylbiguanide, and N,N-dimyristylbiguanide. Other illustrative compounds of the above formula will be apparent from the formula and the above meaning of R.

In the modification of the amphiphiles of formula I wherein n is 1, the compounds are of the formula:

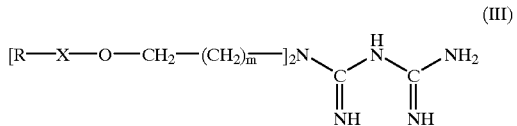

(III)

wherein R, X and m have the previously stated meanings. Such compounds are illustrated by N,N-di(2-(palmitoyloxy)ethyl)biguanide, by N,N-di(2-(oleoyloxy)ethyl) biguanide, and by N,N-di(6-(stearoyloxy)hexyl)biguanide. Other illustrative compounds of formula III will be apparent from the formula and the above meanings of R and m.

For convenience, the amphiphilic compounds of the invention represented by formula II can be viewed as N,N-di-R-biguanide derivatives, and the compounds represented by formula III can be visualized as N,N-di(R-carboxyalkyl)biguanide derivatives, wherein R has the previously stated meaning. The derivatives, however, are not necessarily prepared from biguanide. In general, the compounds of formula III are preferred over the compounds of formula II. Particularly preferred derivatives are those described in the Examples that follow.

There are a number of synthetic techniques in the art that have been developed for the synthesis of biguanides. The method most often used involves the reaction of amine hydrochlorides with dicyanodiamide or its derivatives. Emich, F. *Monatsh. Chem.* 1891 12:5; Curd and Rose, (1946) *J. Chem Soc.* 729; Krentzberger and Tantaway (1977) *Liegis Ann. Chem.* 1625; Warner and Lynch (1979) *J. Med Chem.* 22: 359. Thus, a general synthesis that can be used to produce compounds of the invention involves the conversion of a dialkanolamine to a diacyl derivative (after protecting the amine), deprotection of the amine, and reaction of the resulting secondary amine with dicyanodiamide to produce the desired product. For example, diethanolamine is a suitable starting material. After protection of the amine group of diethanolamine with the acid labile tert-butoxycarbonyl (BOC) protective group, acylation with the appropriate fatty acid chloride and removal of the BOC group by treatment with 4M HCl in dioxane, the resulting hydrochloride is reacted with dicyanodiamide in n-butanol at 110° C.

The initial dialkanolamine can be obtained commercially (diethanolamine is commercially available and is inexpensive) or can be synthesized according to published methods, for example, dialkylation reactions for the production of secondary amines from hydroxy-protected omega-hydroxyalkylhalides. Omega-hydroxyalkylhalides are themselves available from the corresponding alpha, omega-dihydroxyalkanes, which can be prepared from cycloalkenes by oxidation (e.g. with ozone) and reduction. The acyl groups are available from the acid halides (or anhydrides) of the corresponding carboxylic acids, which, as previously indicated, are preferably fatty acids and thus available commercially.

The cationic lipids of the invention are useful as carriers for various biological molecules, such as antibiotics or nucleic acids. In particular, the cationic lipids can be used alone or in combination with other lipids in formulations for the preparation of lipid vesicles or liposomes for use in intracellular delivery systems. See Lasic, D., *Liposomes: From Physics to Applications,* Elsevier: Amsterdam, 1993. Uses contemplated for the lipids of the invention include both in vivo and in vitro transfection procedures corresponding to those presently known that use amphiphilic lipids, including those using commercial cationic lipid preparations, such as Lipofectin™, and various other published techniques using conventional cationic lipid technology and methods. The cationic lipids of the invention can be used in pharmaceutical formulations to deliver therapeutic agents by various routes and to various sites in an animal body to achieve a desired therapeutic effect.

Compositions of the present invention will be usable in the manner described for other known cationic lipids, although optimization of operating parameters will improve results, using the specific information provided for compounds of the invention is this specification along with the knowledge of a person of skill in the arts of lipid preparation and use. A reader unfamiliar with this background information is referred to the publications under the heading Relevant Literature above and, in particular, to PCT patent application numbers WO 96/40962 and WO 96/40963. These last-cited patents describe a number of therapeutic formulations and methods in detail, including examples of the use of specific cationic lipids (different from those described here) that can be followed substantially be substituting the cationic lipids of the present invention for those described.

The lipids of the present invention are particularly useful and advantageous in the transfection of animal cells by genetic material. Genetic material is intended to include both DNA and RNA. RNA of interest includes antisense RNA or ribozymes which, upon delivery to the target cell, interfere with a cellular process, e.g. a cancer cell or virus-infected cell. Introduced RNA may also include mRNA which is translated to produce a peptide of interest upon introduction into the target cell. DNA of interest includes any DNA coding for a therapeutic or prophylactic, e.g. vaccine, peptide, as well as a DNA that codes for an RNA as the active species, e.g. ribozyme or antisense. DNA of interest also includes DNA coding for a cellular factor which, when expressed, activates the expression of an endogenous gene.

Usually, a cationic lipid of the invention will be used with a non-cationic lipid or helper lipid. The non-cationic lipid will usually be a neutral lipid, but could also be an anionic lipid. The choice of helper lipid will depend on a number of proactical considerations, including the target cells to be transfected, whether the transfection will be done in vitro or in vivo, stability of the resulting lipid bilayer, mode of delivery, etc. DOPE is advantageously used as a helper lipid for in vitro transfections because of its fusogenic properties as part of a lipid carrier. Cholesterol or DLPE are preferably used as helper lipids for in vivo delivery. A lipid carrier is intended to mean a cationic amphiphile of the invention together with any additional lipids, typically a neutral lipid such as DOPE, DLPE or cholesterol, and includes liposomes, micelles, interleaved bilayers of lipid and the like.

The cationic lipids of the invention will generally be mixed with a helper lipid in a molar ratio of from 3:1 to 1:3, preferably 1:1, in chloroform. The mixture is dried, and rehydrated in, e.g., 5% dextrose in water or a physiologic buffer to form liposomes. Preferable, low ionic strength solutions are used. The resulting liposomes may be used directly or, preferably, sonicated or extruded through membranes having a pore size ranging from 50 to 600 nm to reduce the size of the liposomes. Preferably, the liposomes are extruded through a series of membranes having decreasing pore sizes, e.g., 600 nm, 200 nm and 50 nm.

The resulting liposomes are mixed with a nucleic acid solution with constant agitation to form the lipid-nucleic acid complexes. Selection of appropriate cationic and neutral lipids will depend on physical properties, including the ability to hydrate and form liposomes, ease in manipulation, stability of resulting liposomes and complexes etc. Those that form suitable lipid-nucleic acid complexes may then be assessed at various lipid-nucleic acid ratios and concentrations for their ability to transfect the desired target cell types. While a range of lipid-nucleic acid complex formulations are effective in cell transfection, optimum conditions are determined empirically in the desired experimental system.

Non-lipid material, (such as biological molecules being delivered to an animal or plant cell or target-specific moieties) can be conjugated through a linking group to one or more hydrophobic groups, e.g., using alkyl chains containing from about 12 to 20 carbon atoms, either prior or subsequent to vesicle formation. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, as the literature provides a great variety of such methods. Alternatively, some compounds will have hydrophobic regions or domains which will allow their association with the lipid mixture without covalent linking to one or more lipid groups.

For the most part, the active compounds to be bound to the lipid mixture are ligands or receptors capable of binding to a biological molecule of interest. For example, a ligand binding specifically to a receptor on a particular target cell type can be used to target delivery of the lipid carrier (with, e.g., the DNA or antibiotic of interest) to the desired target cells. Alternatively, the active compound may be a peptide or other small molecule designed to regulate intracellular trafficking of the delivered substance, e.g., triggering endosomal release or transport into the nucleus using a nuclear localizing sequence.

The active compounds bound to the lipid mixture can vary widely, from small haptens (having molecular weights of about 125 to 2000 daltons) to antigens (having molecular weights ranging from around 6000 to 1 million daltons). Of particular interest are proteinaceous ligands that bind to and are internalized by specific complementary binding partners on cell surfaces. Illustrative active compounds include cytokines, interferons, hormones, antibodies to cell surface receptors or other molecules, and fragments of such compounds that retain the ability to bind to the same cell surface binding partners that bind the original (non-fragmented) molecules.

The number of active compounds bound to a lipid carrier will vary with the size of the complex, the size of the compound, the binding affinity of the molecule to the target cell receptor or ligand, and the like. Usually, the bound active molecules will be present in the lipid mixture in from about 0.001 to 2 mole percent, more usually from about 0.01 to 1 mole percent based on the percent of bound molecules to the total number of molecules available in the mixture for binding.

The cationic amphiphiles are particularly useful as carriers for anionic compounds, particularly polyanionic macromolecules such as nucleic acids. Where the amphiphiles are intended for use in vivo, particularly in vivo in humans, or where repeat administration is necessary, the carriers should be screened for toxicity. The effects of such cationic amphiphiles in vivo can be demonstrated in animal experiments. An animal, such as a mouse, can be administered one or more doses of material containing between 10 nm and 10 μm of the lipid to be tested, typically complexed with the intended active component (such as DNA). At various times after administration the animals are monitored for evidence of toxicity, e.g. lethargy or inflammation. The animals are sacrificed and the liver examined for toxicity. Total lipid is also advantageously analyzed for the particular cationic lipid or its partial degradation product using, e.g., HPLC.

The cationic amphiphiles are positively charged, and a tight charge complex can be formed between a cationic lipid carrier and a polyanionic nucleic acid, resulting in a lipid carrier-nucleic acid complex that can be used directly for transfection in vitro or for delivery to a mammal for transfection in vivo. Delivery can be by any means known to persons of skill in the art, e.g., systemic, intraperitoneal, intratracheal, intranasal, intramuscular, etc. PCT patent application WO 96/40962 describes the preparation and use of cationic lipid carriers for in vivo DNA delivery. For aerosol administration, via intranasal or intraoral delivery, the lipid-DNA complex will withstand both the forces of nebulization and the environment within the lung airways and be capable of transfecting lung cells. Techniques for delivering genes via aerosol administration of lipid-DNA complexes are described in PCT patent application WO 93/12756.

For in vivo or in vitro gene delivery, various lipid formulations may be assessed for optimal transfection of the target cells of interest. Thus, various cationic lipids of the present invention are tested in combination with different neutral lipids, and the lipid mixtures complexed with DNA in multiple different ratios, generally ranging from about 6:1 to 1:20 μgDNA:nanomoles cationic lipid. For in vitro transfections, the various combinations are tested for their ability to transfect target cells using standard molecular biology techniques to determine DNA uptake, RNA and/or protein production. For in vivo gene delivery, lipid carrier compositions may be evaluated by their ability to deliver a reporter gene (e.g. CAT which encodes chloramphenicol acetyltransferase) to a given tissue in an animal, such as a mouse.

Particular cells can be transfected by the use of particular cationic lipids for preparation of the lipid carriers, for example, by the use of EDMPC to deliver genes to lung cells (WO 96/40963), or by altering the lipid-DNA formulation to preferentially transfect the desired cell types (WO 96/40962). Thus, for example, in circumstances where a negatively charged complex is desired, relatively less cationic lipid will be complexed to the DNA resulting in a higher DNA-cationic lipid ratio. Conversely, in circumstances where a positively charged complex is desired, relatively more cationic lipid will be complexed with the DNA, resulting in a lower DNA-lipid ratio. To avoid precipitation, which generally occurs around charge neutrality, net positively charged complexes are generally prepared by adding DNA to the liposomes, and net negatively charged complexes are prepared by adding liposomes to the DNA, in either case with constant agitation.

A particular site-directing ligand or antibody can be conjugated to the lipid carrier in accordance with conventional techniques, either by conjugating the site-directing molecule to a lipid for incorporation into the lipid bilayer or by providing a linking group on a lipid present in the bilayer for linking to a functionality of the site-directing compound. Such techniques are well known to those skilled in the art.

The various lipid-nucleic acid complexes are prepared by known methods, for example, as described in PCT application numbers WO 95/14381 and WO 96/40962. Precipitation of resultant lipid-DNA mixtures is determined by visual inspection. While precipitation does not preclude the use of such complexes for in vitro transfection purposes, precipitated complexes are not desirable for in vivo transfection. To make the lipid-DNA complexes more visible, the complexes can be stained with a dye that does not itself cause aggregation, but which will stain either the DNA or the lipid. For example, Sudan black (which stains lipid) can be used as an aid to examine the lipid-DNA mixture to determine if aggregation has occurred. Particle size can be studied by methods known in the art including, for example, electron microscopy, laser light scattering, Coulter™ counting/sizing, and the like. Standard-size beads can be used for calibration to determine the size of liposomes or complexes that are formed.

Generally, the nucleic acid material is mixed with suspensions of preformed liposomes, which may be multilamellar vesicles (MLVs), large unilamellar vesicles (LUVs), or small unilamellar vesicles (SUVs), preferably SUVs formed by extruding the liposomes through a membrane having a pore size in the range of 50 to 400 nm. Preformed liposomes are mixed with DNA essentially as described in WO 96/40962. In preparing the lipid-DNA complex for nebulization, relatively smaller complexes are desired, since larger complexes will undergo more shearing during the nebulization process. See WO 96/40963.

The following examples are offered by way of illustration and not by way of limitation.

EXAMPLES

Example 1. General Synthesis Scheme

Biguanides are prepared according to the following general scheme.

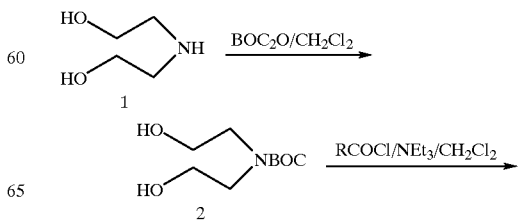

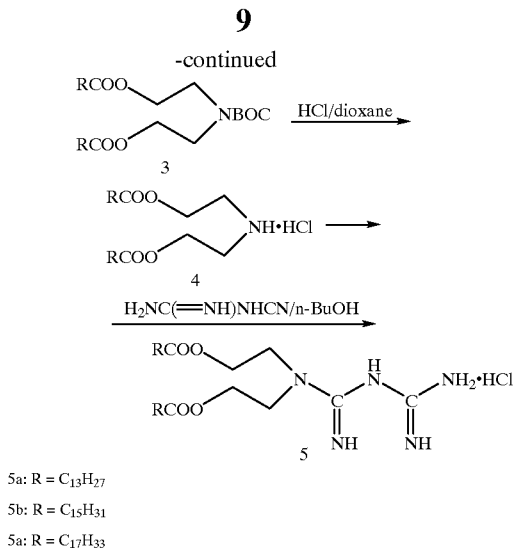

5a: R = C$_{13}$H$_{27}$
5b: R = C$_{15}$H$_{31}$
5a: R = C$_{17}$H$_{33}$

Commercially available diethanolamine was protected on nitrogen using di-tert-butyl-pyrocarbonate, acylated with the appropriate acyl chloride, the N-BOC protection group was cleaved with 4M HCl in dioxane, and the resulting hydrochloride was reacted with dicyanodiamide in n-butanol to yield the desired biguanide.

Example 2. Preparation of lipophilic biguanides. Synthesis of dioleoyl biguanide (a) N-BOC diethanolamine 2.

To a solution of 10 ml (0.1 mol) diethanolamine in 150 ml of acetonitrile was added 22.8 g (0.105 mol) of di-tert-butyl-pyrocarbonate and the mixture was stirred overnight at room temperature. The resulting solution was evaporated, the residue dissolved in ethyl acetate/hexane (7:3 (v/v)) and passed through a plug of silica. Evaporation of the solvent yielded 16.4 g (80%) N-BOC diethanolamine.

(b) N-BOC ester 3.

3.4 ml (0.024 mol) of triethylamine was added to a solution of 2.0 g (0.0097 mol) of 2 in 100 ml CH$_2$Cl$_2$ at 0° C. Then, in 10 min with stirring was added 6.5 ml (0.02 mol) oleoyl chloride. The mixture was stirred at 0° C. for 30 min, then at room temperature for 45 min. The resulting solution was washed with 10% citric acid (2×50 ml), with 10% aqueous solution of sodium bicarbonate (2×50 ml), dried over MgSO$_4$, filtered, the filtrate evaporated on a rotavapor, and the rest was chromatographed on a silica gel using 0–15% EtOAc/hexane to get 6.9 g (94%) of N-BOC ester 3.

(c) Amine 4.

20 ml of a 4M solution of HCl in dioxane was added to 3.5 g (0.086 mol) of N-BOC ester 3, and the mixture was stirred at room temperature for 2 hours. The resulting suspension was evaporated on a rotavapor, diluted with ether (50 ml), filtered, washed with ether (2×25ml) and dried under vacuum to yield 3.3 g (97%) of amino ester 4.

(d) Biguanide 5.

To 1.5 g (0.0022 mol) of amino ester 4 hydrochloride were added 0.56 g (0.0067 mol) of dicyanodiamide and 5.0 ml of n-butanol. The resulting mixture was stirred at 110° C. for 2 hours. Completion of the reaction was monitored by TLC (Merck F$_{254}$ silica gel on glass baked plates; developing solvent: 20% MeOH/80% CHCl$_3$; spots were visualized by spraying the TLC plate with 4% ethanolic solution of phosphomolybdic acid, and heating it on a hot plate at 150° C. for 10 min). The cooled mixture was diluted with 100 ml of CHCl$_3$, washed twice with 5% aqueous NaCl:MeOH/1:1, dried over anhydrous Na$_2$SO$_4$, and evaporated on a rotavapor. The residue was purified on a silica gel column using 1–20% MeOH in CHCl$_3$ as the eluant. After evaporation, 0.78 g (49% yield) of dioleoyl biguanide (DOBG) was obtained as a colorless waxy solid.

Dimyristoyl biguanide (DMBG) (48% yield) and dipalmitoyl biguanide (DPBG) (46% yield) were also prepared using the procedure described above. All structures were confirmed using $^1$H NMR (300 Mhz, CDCl$_3$), and elemental analysis. Representative data:

DOBG 5a: $^1$H NMR (300 MHz, CDCl$_3$) δ0.88 (m, 6 H), 1.27, 1.30 (each m, 40 H), 1.73 (m, 4 H), 2.00 (m, 8 H), 2.30 (m, 4 H), 3.73 (m, 4 H), 4.26 (m, 4 H), 5.33 (m, 4 H), 6.68, 7.38 (each br s, 5 H); $^{13}$C NMR (75.5 MHz, CDCl$_3$) δ173.69, 159.39, 158.26, 129.91, 129.60, 62.34, 48.50, 34.09, 31.86, 29.71, 29.48, 29.27, 29.23, 29.14, 27.17, 24.79, 22.63, 14.06. Anal. Calcd. for C$_{42}$H$_{79}$N$_5$O$_4$·HCl: C, 66.89; H, 10.48; N, 9.29. Found: C, 66.78; H, 10.73; N, 9.20.

DPBG 5b: $^1$H NMR (300 MHz, D$_2$O) δ0.84 (m, 6 H), 1.22 (m, 48 H), 1.50 (m, 4 H), 2.26 (m, 4 H), 3.59 (m, 4 H), 4.12 (m, 4 H); Anal. Calcd. for C$_{38}$H$_{75}$N$_5$O$_4$·HCl: C, 66.89; H, 10.48; N, 9.29. Found: C, 66.78; H, 10.73; N, 9.20.

DMBG 5c: $^1$H NMR (300 MHz, D$_2$O) δ0.89 (m, 6 H), 1.27 (m, 40 H), 1.61 (m, 4 H), 2.35 (m, 4 H), 3.79 (m, 4 H), 4.34 (m, 4 H); Anal. Calcd. for C$_{34}$H$_{67}$N$_5$O$_4$·HCl: C, 63.21; H, 10.33; N, 10.84. Found: C, 62.37; H, 10.49; N, 11.78.

Example 3. Transfection using cationic lipid complexes containing lipophilic biguanide derivatives The biguanide derivatives were tested as carriers for gene transfer and expression in mice. The plasmid p4119 containing the CAT reporter gene under the control of the HCMV promoter was used in the intravenous studies; the plasmid pMB10 containing the lacZ gene under the control of the HCMV promoter was used in the intramuscular studies (see, PCT application WO 96/40962). DOTIM:cholesterol DNA complexes were used as a positive control for intravenous gene delivery; naked DNA was used as a positive control for intramuscular gene delivery.

DOBG, DMBG and DPBG were used to prepare liposomes with either cholesterol or DLPE (1,2-dilauroyl-sn-glycerol-3-phosphoethanolamine) as neutral lipids. The lipids were dissolved in a mixture of chloroform and methanol (1:1). Lipid films of cationic and neutral lipid at a 1:1 molar ratio were formed with a rotary evaporator. The films were hydrated with either 5% dextrose in water (D5W) or 5 mM HEPES buffer (pH 7.4) at various temperatures. DMBG:cholesterol was hydrated with D5W at 50° C.; the resulting liposomes were difficult to extrude through a 0.1 μm membrane. DMBG:DLPE was hydrated in D5W at 50° C. and extruded through a 0.05 μm membrane. DPBG with either DLPE or cholesterol could not be completely hydrated at 50° C. DOBG:cholesterol and DOBG:DLPE were hydrated in D5W at room temperature and extruded through a 0.05 μm membrane.

DNA-liposome complexes were prepared at a 1:10 DNA::cationic lipid ratio (mg DNA:μmole cationic lipid) by adding the DNA, in a solution having a concentration of 0.625 mg/ml DNA in D5W, to the solution of liposomes, in an equal volume, with constant stirring, using a Hamilton Dilutor 540B (Hamilton, Reno, Nev.). The resulting complexes were sized using a Nicomp Submicron Particle Sizer 370 (Nicomp, Santa Barbara, Calif.). Complex sizes ranged from 80 nm to 180 nm for the 3:1 formulations, and from 200 nm to 400 nm for the 1:10 formulations.

ICR female mice (25 g) were used for the in vivo studies. The 1:10 formulations were tested for IV gene delivery. A total of 5 mice were tested per group. A dose of 62.5 μg p4119 plasmid DNA in 200 μl D5W was injected by tail vein per mouse. The lung, heart, liver, and spleen were harvested after 24 h and assayed for CAT activity. Each organ was homogenized in 1.0 ml of a solution of 5 mM EDTA/0.25M Tris-HCl pH 7.8 containing 5 μg/ml Aprotinin (Boehringer Mannheim, Indianapolis, Ind.), 5 μg/ml Leupeptin (Boehringer Mannheim, Indianapolis, Ind.), and 5 mM PMSF (Boehringer Mannheim, Indianapolis, Ind.). The resulting extracts were centrifuged and aliquots of the supernatant were removed for protein analysis, utilizing a bicinchoninic acid based reagent kit (Pierce, Rockford, Ill.). The remaining supernatant was heat treated at 65° C. for 15 min. The CAT activity assay was performed using 5 μl of heat treated supernatant, 25 μl of 125 μg/ml n-Butyryl CoA (Sigma, St. Louis, Mo.), 50 μl of 5 uCi/ml $^{14}$C-chloroamphenicol (DuPont NEN, Boston, Mass.), and 50 μl of 0.25M Tris-HCl/5 mM EDTA. Samples were incubated at 37° C. for 2 h. An addition of 300 μl of mixed xylenes (Aldrich, Milwaukee, Wis.) was made followed by vortexing and centrifugation at 14K rpm for 5 min. The xylene layer was then transferred into 750 μl of 0.25M Tris-HCl/5 mM EDTA, vortexed, and centrifuged at 14 K rpm for 5 min. The upper organic phase was then transferred into scintillation vials containing 5 ml of Ready Safe Liquid Scintillation Cocktail (Beckman, Fullerton, Calif.). Samples were counted for 1 min each. The results are shown in Table 1.

TABLE 1

Gene Transfer Efficiency by Intravenous Delivery

| Formulation (1:1 molar ratio) | DNA/Liposome Ratio (μg/nM) | Relative Activity[1] | Toxicity (Lung) (5 mice/group) |
|---|---|---|---|
| DMBG/Chol | 1:10 | 1.06 | 1 dead, 2 lethargic |
| DMBG/DLPE | 1:10 | 6.02 | 1 dead, 4 lethargic |
| DOBG/Chol | 1:10 | 3.42 | 4 dead |
| DOBG/DLPE | 1:10 | 4.48 | 5 lethargic, 2 liver spots |

[1]Relative activity is calculated as the ratio: New formulation/Positive Control (DOTIM/Cholesterol)

The 1:3 formulations were tested for IM gene delivery. Three animals were tested per group. Each mouse was injected in the rectus femoris muscles of both legs with a dose of 31.25 μg pMB10 plasmid DNA in D5W. The muscles were harvested 48 h after dosing and analyzed for β-gal expression using a CPRG based activity assay. Samples were homogenized in 1 ml of 0.25M Tris-HCl/5 mM EDTA containing 10 μg/ml Aprotinin (Sigma, St. Louis, Mo.), 100 μM TPCK (N-tosyl-L-phenylalanine chloromethyl ketone, Sigma, St. Louis, Mo.), and 100 μM TLCK (Nα-p-tosyl-L-lysine chloromethyl ketone, Sigma, St. Louis, Mo.). The extracts were then centrifuged at 14K rpm for 10 min. Supernatants were diluted 1:2 in 0.25M Tris-HCl/5 mM EDTA in 96-well microtiter plates (Costar, Cambridge, Mass.) previously coated with mouse anti-E. coli B-galactosidase mAb. Plates were incubated for 1 h at room temperature and washed with PBS containing 0.2% Tween-20 (Sigma, St. Louis, Mo.). CPRG substrate cocktail containing 2.5 mg/ml CPRG (Boehringer Mannheim, Indianapolis, IN), 1.8 mg/ml MgCl$_2$, and 7.5 μl/ml of 2-mercaptoethanol was added at 100 μl/well. The plates were incubated at 37° C. for 2 h and read on a 96 well ThermoMax microtiter plate reader (Molecular Devices, Sunnyvale, Calif.). Additionally, supernatants were assayed for protein utilizing a bicinchoninic acid based reagent kit (Pierce, Rockford, Ill.). The results are shown in Table 2.

TABLE 2

Gene Transfer Efficiency by Intramuscular Delivery

| Formulation (1:1 molar ratio) | DNA/Liposome (μg:nM) | Relative Activity[1] |
|---|---|---|
| DMBG/Chol | 3:1 | 0.6 |
| DOBG/Chol | 3:1 | 0.5 |

[1]Relative activity is calculated as the ratio: New formulation/Positive Control (naked DNA)

The cationic lipids DMBG and DOBG, when used with either cholesterol or DLPE as neutral lipids, showed transfection activity in the lung comparable to or higher than DOTIM:cholesterol by IV administration. The other organs tested showed considerably less expression of the reporter gene. As compared to DOTIM:cholesterol, the relative activities in the lung of DMBG:DLPE and DOBG:DLPE were 6 and 4.5 respectively. Formulations of the same lipids with DLPE instead of cholesterol also showed higher transfection activity (relative activities of 3 and 1 respectively) than the DOTIM:cholesterol transfections. All of the formulations tested intravenously were toxic to some degree, with the DOBG:cholesterol formulation being the most toxic. Toxicity can be modulated by the choice of neutral lipid used in the formulation, as can be seen by comparing use of cholesterol or DLPE with the same cationic lipid. Lower toxicity would be expected at lower lipid:DNA doses, and could be further modulated by use of protective agents, e.g., a steroid such as dexamethasone, administered in conjunction with delivery of the lipid:DNA complexes. DMBG:cholesterol and DOBG:cholesterol had lower relative activity than naked DNA when injected intramuscularly (relative activities of 0.6 and 0.5, respectively).

The biguanide derivatives of the present invention differ from the guanidine derivatives described in WO 95/14381 in the positively charged headgroups. The positive charge of the biguanide derivatives is delocalized over five nitrogen atoms, whereas the positive charge of the guanidine derivatives is delocalized over three nitrogen atoms. Thus, compounds of the present invention have been compared to the guanidine derivatives having the identical hydrophobic chains (not shown). In formulations with cholesterol, the dimyristoyl derivatives of guanidine have a higher in vivo transfection activity than the dimyristoyl derivatives of biguanide. The dioleoyl derivatives of biguanide, however, have a higher in vivo transfection activity than the dioleolyl derivatives of guanidine. Thus, the degree of delocalization does not seem to correlate directly to transfection activity in vivo.

All publications and patent applications cited herein are hereby incorporated by reference to the same extent as if fully set forth herein.

The invention now being fully described, it will be apparent to one of ordinary skill in the art that many changes and modifications can be made thereto without departing from the spirit or scope of the appended claims.

We claim:

1. A compound of the formula:

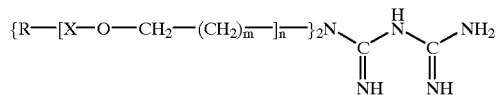

wherein each R independently is a straight-chain or branched-chain, aliphatic hydrocarbyl group of 5 to 29 carbon atoms inclusive, each X is —CH$_2$— or —CO—, each m is an integer from 0 to 7 inclusive and each n is zero or 1, with the proviso that when n is 1, the total number of carbon atoms in R and —(CH$_2$)$_m$— is at least 10, and when n is zero, each R independently is a straight-chain or branched-chain, aliphatic hydrocarbyl group of at least 10 carbon atoms inclusive.

2. The compound of claim 1 wherein n is zero.

3. The compound of claim 2 wherein each R independently has from 14 to 24 carbon atoms inclusive.

4. The compound of claim 1 wherein R is myristoyl.

5. The compound of claim 1 wherein R is lauroyl.

6. The compound of claim 1 wherein R is oleoyl.

7. The compound of claim 1 wherein n is 1.

8. The compound of claim 7 wherein m is 1.

9. A method of transfecting a mammalian cell comprising contacting the cell with a lipid-nucleic acid complex comprising the compound of claim 1, thereby resulting in the entry of the complex into the cell.

10. The method of claim 9 wherein said contacting is performed in vitro.

11. The method of claim 9 wherein said contacting is performed in vivo.

12. A method for delivering a biological composition to cells in a tissue of a mammal comprising:

contacting said cells with a complex comprising said composition and a cationic amphiphile of the formula

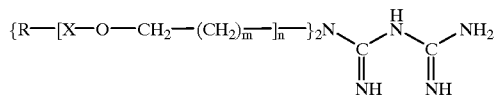

wherein each R independently is a straight-chain or branched-chain, aliphatic hydrocarbyl group of 5 to 29 carbon atoms inclusive, each X is —CH$_2$— or —CO—, each m is an integer from 0 to 7 inclusive and each n is zero or 1, with the proviso that when n is 1, the total number of carbon atoms in R and —(CH$_2$)$_m$— is at least 10, and when n is zero, each R independently is a straight-chain or branched-chain, aliphatic hydrocarbyl group of at least 10 carbon atoms inclusive, wherein said complex provides for entry of said composition into said cells.

13. The method of claim 12 wherein said contacting is performed ex vivo.

14. The method of claim 12 wherein said contacting is performed in vivo.

15. The method of claim 12 wherein said complex further comprises a neutral lipid.

16. The method of claim 15 wherein the neutral lipid is selected from the group consisting of cholesterol, DOPE and DLPE.

17. The method of claim 15 wherein the neutral lipid is cholesterol.

18. A method of transforming a mammalian cell comprising:

contacting a polynucleotide with a lipid comprising a positively-charged headgroup of the formula

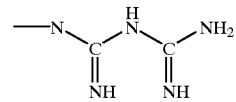

to form a polynucleotide-lipid complex;

contacting said polynucleotide-lipid complex with said mammalian cell; thereby resulting in the entry of the complex into said mammalian cell.

19. The method of claim 18 wherein the mammalian cell transformation takes place in vivo.

20. The method of claim 19 wherein the polynucleotide-lipid complex is administered to a mammal by intravenous administration.

21. The method of claim 19 wherein the polynucleotide-lipid complex is administered intramuscularly.

* * * * *